(12) United States Patent
Wilson et al.

(10) Patent No.: US 10,945,687 B2
(45) Date of Patent: Mar. 16, 2021

(54) DISPLAY DEVICE FOR REDUCING RADIATION EXPOSURE TO MEDICAL PERSONNEL

(71) Applicant: Egg Medical, Inc., Maple Grove, MN (US)

(72) Inventors: Robert F. Wilson, Roseville, MN (US); John P. Gainor, Mendota Heights, MN (US); James Montague, Elk River, MN (US); Uma S. Valeti, St. Paul, MN (US)

(73) Assignee: Egg Medical, Inc., Arden Hills, MN (US)

( * ) Notice: Subject to any disclaimer, the term of this patent is extended or adjusted under 35 U.S.C. 154(b) by 0 days.

(21) Appl. No.: 16/055,749

(22) Filed: Aug. 6, 2018

(65) Prior Publication Data

US 2019/0038241 A1 Feb. 7, 2019

Related U.S. Application Data (60) Provisional application No. 62/541,367, filed on Aug. 4, 2017.

(51) Int. Cl.

| | | |
|---|---|---|
| A61B 6/10 | (2006.01) | |
| A61B 6/00 | (2006.01) | |
| G21F 7/02 | (2006.01) | |
| A61N 5/10 | (2006.01) | |
| G21F 3/00 | (2006.01) | |
| A61B 6/04 | (2006.01) | |

(52) U.S. Cl.
CPC .............. *A61B 6/107* (2013.01); *A61B 6/462* (2013.01); *A61B 6/463* (2013.01); *A61B 6/465* (2013.01); *A61B 6/548* (2013.01); *G21F 7/02* (2013.01); *A61B 6/0407* (2013.01); *A61B 6/487* (2013.01); *A61N 2005/1094* (2013.01); *G21F 3/00* (2013.01)

(58) Field of Classification Search
CPC ................................. A61B 6/10; A61B 6/107
See application file for complete search history.

(56) References Cited

U.S. PATENT DOCUMENTS

| | | | | |
|---|---|---|---|---|
| 8,338,810 | B2 * | 12/2012 | Hoernig | A61B 6/107 |
| | | | | 250/505.1 |
| 8,876,380 | B2 * | 11/2014 | Mizrahi | A61B 5/0422 |
| | | | | 378/203 |
| 10,016,251 | B2 * | 7/2018 | Holman | A62B 17/04 |
| 10,172,576 | B2 * | 1/2019 | Shealy | A61B 6/0407 |
| 2003/0091152 | A1 | 5/2003 | Dietz et al. | |

(Continued)

FOREIGN PATENT DOCUMENTS

CN 203195765 U 9/2013

OTHER PUBLICATIONS

WIPO, U.S. International Search Authority, International Search Report and Written Opinion dated Oct. 22, 2018 in International Patent Application No. PCT/US2018/045350, 9 pages.

*Primary Examiner* — Thomas R Artman
(74) *Attorney, Agent, or Firm* — Inskeep IP Group, Inc.

(57) ABSTRACT

A transparent radiation shield, attachable to a patient support platform, and movable to shield a physician from imaging radiation, includes a transparent computer display that is controllable to provide a data overlay on the shield pertaining to patient data and/or x-ray images.

18 Claims, 6 Drawing Sheets

(56) References Cited

U.S. PATENT DOCUMENTS

| | | | |
|---|---|---|---|
| 2012/0051520 A1* | 3/2012 | Hoernig | A61B 6/107 378/98.5 |
| 2012/0105306 A1 | 5/2012 | Fleck | |
| 2012/0163544 A1* | 6/2012 | Mizrahi | A61B 5/748 378/98.2 |
| 2013/0072787 A1* | 3/2013 | Wallace | A61B 6/12 600/424 |
| 2015/0362736 A1 | 12/2015 | Kowasic | |
| 2017/0000580 A1* | 1/2017 | Holman | G02B 27/0172 |
| 2017/0004895 A1* | 1/2017 | Holman | G02B 27/0172 |
| 2017/0119324 A1 | 5/2017 | Wilson et al. | |
| 2018/0235555 A1* | 8/2018 | Shealy | A61B 6/0407 |
| 2019/0038241 A1* | 2/2019 | Wilson | A61B 6/548 |

\* cited by examiner

DISPLAY DEVICE FOR REDUCING RADIATION EXPOSURE TO MEDICAL PERSONNEL

RELATED APPLICATIONS

This application claims priority to U.S. Provisional Application Ser. No. 62/541,367 filed Aug. 4, 2017 entitled Display Device for Reducing Radiation Exposure to Medical Personnel, which is hereby incorporated herein by reference in its entirety.

BACKGROUND OF THE INVENTION

Radiation exposure for healthcare workers in radiology and cardiology interventional laboratories poses a significant health risk. In one study of cardiology healthcare workers stationed in cardiac catheterization laboratories where x-rays are routinely used for medical procedures (such as angiography, heart biopsy, pacemaker placement, transcatheter stent or heart valve placement, radiofrequency ablation of heart rhythm disorders and right heart catheterization), the risk of cancer was found to be increased three-fold compared to similar workers in areas where radiation is not used. These findings are discussed in Andreassi M G, Piccaluga E, Guagliumi G, et al. Occupational health risks in cardiac catheterization laboratory workers. Circ Cardiovasc Interv. 2016; April; 9(4):e003273; and also in Andreassi M G, Piccaluga E, Guagliumi G, et al. Subclinical carotid atherosclerosis and early vascular aging from long-term low-dose ionizing radiation exposure: a genetic, telomere, and vascular ultrasound study in cardiac catheterization laboratory staff. JACC Cardiovasc Interv. 2015 Apr. 20; 8(4):616-27.

Devices to shield worker from x-ray photons are widely used. These vary from x-ray blocking garments worn by workers to shields that hang from the ceiling or rails on the x-ray table or are rolled around the room on a trolley. An ideal shield would be easily positioned from within the sterile field to cover the area of the body being accessed by the physician, allow the physician's hands to work on the body, permit the physician to visually see the operating field, and move with the patient as the table is repositioned. Although many shields are constructed from x-ray blocking material that transmits the visible light spectrum, these shields are usually attached to the ceiling, roll on the floor, or are attached to the fixed portion of the x-ray table (attached to metal rails on the side of the table). As a result, the shield does not move as the mobile part of the x-ray table is repositioned. In addition, it has been virtually impossible to protect physicians doing procedures next to the patient's chest or at their head while still allowing visualization and access to the operative field.

In addition to the above characteristics of an ideal radiation shield, an overlay of data (such as blood pressure, heart rate, arterial oxygen saturation, or electrocardiogram) or images (such as live ultrasound images or x-ray images) would allow the physician to be informed of the condition of the patient without having to look away from the operating field.

OBJECTS AND SUMMARY OF THE INVENTION

The invention described herein relates to a repositionable radiation shield device that is transparent, allowing the surgeon to view the operating field while the surgeon's head and upper chest are protected from scatter radiation. This shield may be easily moved into position by the physician or lab staff from within the sterile field to obtain optimal patient visualization and radiation protection based on the anatomy of the patient being accessed and the position of the physician. Attached to the transparent shield is a display that, when activated, may turn from transparent to opaque or partially transparent shield, allowing the superimposition of data, such as images, physiologic parameters, instructions, image guidance for surgery, or other medical information. Alternatively, the shield may have multiple components, with a clear shield component for viewing the patient and separate non-transparent displays arrayed on the shield to provide patient data. Attached to the shield can also be other features that allow the surgeon to view the operating field better or with added information or images. These features include, but are not limited to the following:

Lighting is used to illuminate the area being viewed through the shield. The frequency spectrum of the emitted light may vary from infra-red to ultraviolet to illuminate different structures preferentially.

A camera attached to the shield display similarly can allow the surgeon to view the field and, in one embodiment, overlay the imaged field on the shield display. The imaging camera can image at varied frequency spectrums, allowing the surgeon to see various aspects of the field, such as bleeding, temperature differences (such as the heat related to bleeding under the skin), arterial and venous blood flow, and surface contamination (such as using ultraviolet imaging). In addition, such imaging display on the shield could be used in conjunction with other methods described previously, such as fluorescein perfusion imaging.

The camera display image can also be co-registered to the operating field, such that the image overlays the visual view of the field seen by the operator through the semi-transparent display. Such co-registration can be accomplished by using fiduciary points in the operating field imaged by the camera. The digital image is then manipulated considering the following factors:

The position and angle of the shield relative to the operating field. These factors can be calculated from the camera image of fiduciary points in the operating field, where the points have known positions in space relative to each other. This can be accomplished in a number of ways, including placing a sterile set of three or more physically-connected fiduciary points in the field, a similar marking set, where the points in the field independently or together detect the position and transmit it to a computer, or by the operator identifying by a marking device the position of three or more points with a device that transmits to or is detected by as receiving device that then calculates the position of the markers in space. One additional method to establish fiduciary points and to determine the relationship of the shield display to the imaged surface is to project from the shield display light patterns (such as a grid, cross or crosses, or concentric circles). The geometric distortion of the projected objects can then be used to determine the topography of the imaged field relative to the camera on the shield.

In addition, a "heads-up" display without the need for a display alternating between transparent and opaque can be employed. In this embodiment, information is displayed onto the shield for use by the operator. The display can be switched off and on and can be moved about the screen using a touch panel control or through standard switches.

Control of the shield display in the operating room environment is best accomplished by switches or control mechanisms that cannot be contaminated or that can be easily cleaned. Control can be accomplished by physical switches on the shield, preferably using switches that can be operated though a sterile barrier (such as a clear bag) surrounding the shield display and are easy to wipe clean, such as membrane touch switches. Alternatively, control devices that do not require physical touch can be employed. These include detectors that identify the position of hands (such as ultrasonic, light, capacitive, or magnetic detectors), or any of a variety of touch switches, or a touchscreen membrane that covers the display shield.

The table that patients are lying on during the operation is usually moved in order to x-ray image various parts of the body. To keep the shield in position for the surgeon to view the same part of the body, the shield should move with the patient. In one embodiment, the shield display can be attached to a specialized sled on which the patient lays, an operating table, an x-ray table, or other platform where the shield will move with the patient as the table is moved in and out of the x-ray. The sled contains wiring and electrical power to connect to the display on one end and to the image or data source on the other end. The source can be either a communication cable (such as wired or fiber optic cables) or power supply cable, or a combined cable that is connected to the data source directly, or indirectly (such as through a radiofrequency or infrared connection to the data source).

An additional feature is a touchscreen control device overlaid on the display screen or the radiation shield directly. The touchscreen can be of any type (such as resistive, capacitive, or ultrasonic) such that the touchscreen passes visible light through all or a portion of the surface. The touchscreen is connected as an input device to other devices. Such devices include computer monitors, telecommunications devices, and imaging systems.

An additional modification of the shielding device is to curve the material such that the shield magnifies the operative field. As an example, this would be useful for surgeries involving small devices or small blood vessels. Magnification can be accomplished optically in a number of ways, including through a curved optical medium attached to the display shield, by curving the radiation shield material, or by curving the transparent display material. Magnification can also be accomplished by magnification of the image obtained from the camera and display of that image on the shield display. One advantage of that method is that the amount of magnification can be varied more easily than changing the optical magnification and the field of magnification can be changed without moving the shield.

U.S. Pat. No. 10,106,172 to Wilson et al., and incorporated by reference herein, describes a procedure sled in which the patient lies on a foam-filled carbon fiber shell. The sled described by Wilson et al. has, in one embodiment, rails attached to the outer border of the shell, allowing attachment of devices. In one or more embodiments of the device described herein, the device is mountable to the sled described by Wilson et al. and some of the electronic components are contained within, or attached to the sled.

It is recognized that the addition of a display system described herein would facilitate medical procedures in other environments where x-ray imaging is not used, such as operating rooms or emergency rooms, and would not require x-ray shielding. The ability, however, to operate a display, control or imaging system in a sterile field environment where the display, control, or imaging system moved with the patient facilitates the ability of medical personnel in several ways.

First, the medical personnel would have the ability to read the display and use the control screen while performing surgery on a patient resting on a moving table. Second, the imaging or camera system can maintain a constant view of the imaged field, where the registration of fiduciary points does not change with patient movement. This maintenance of registration permits more accurate image analysis and allows more accurate assessment of the change in the image over time, such as detecting bleeding through changes in skin topography, for example.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Figure 1:
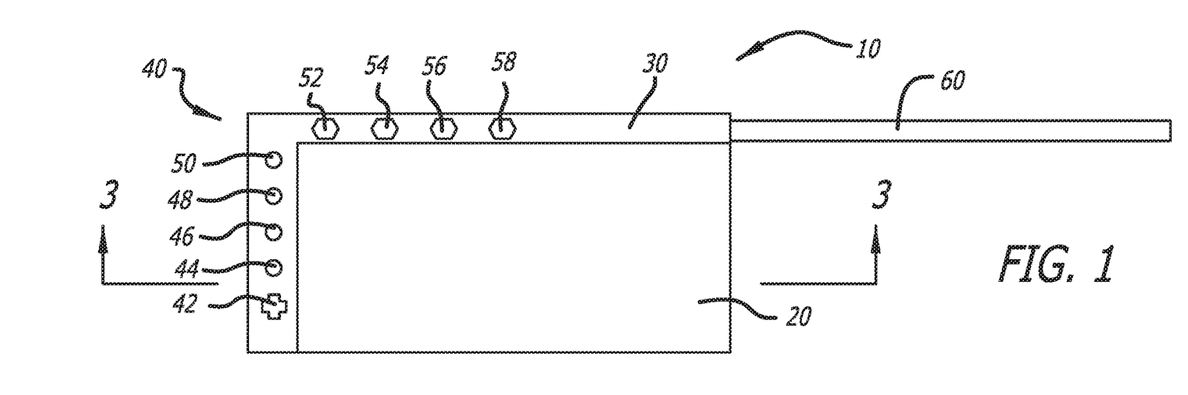
FIG. 1 is a front elevation of an embodiment of a device of the invention.
Figure 2:
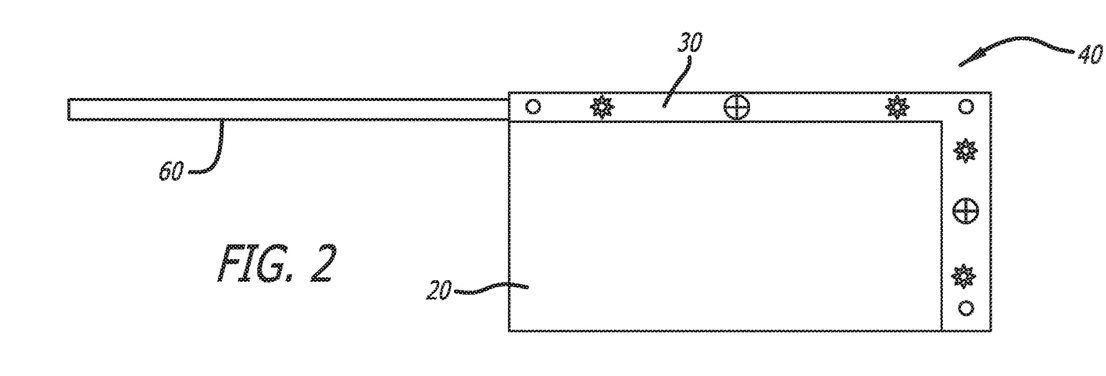
FIG. 2 is a rear elevation of an embodiment of a device of the invention.

Referring now to the figures, and first to FIG. 1, there is shown an embodiment of a shield 10 of the invention. It can be seen that the shield 10 includes a transparent portion 20, through which the patient can be seen, and a control portion 30 that includes a plurality of control switches 40. The control switches 40 control whatever features may be included on the shield. By way of non-limiting example, the embodiment shown in FIG. 1 may includes a display control 42, a display "on" switch 44, an fiduciary point control 46, a field lighting control 48, a camera switch 50, and display source selectors 52, 54, 56 and 58. The switches and controls may be physical buttons and knobs or other mechanical devices, or the shield may include touchscreen controls, as is known in the art. The shield may also be voice-activated. One skilled in the art will understand that the controls and functions provided with the shield 10 may be customizable to the needs of the user. The shield 10 may be attached to an arm 60 that is connectable to a hospital bed, equipment stand, fluoroscope, or the like. FIG. 2 is a back view of the shield 10, and illustrates the transparent properties of the shield 10.

Figure 3:
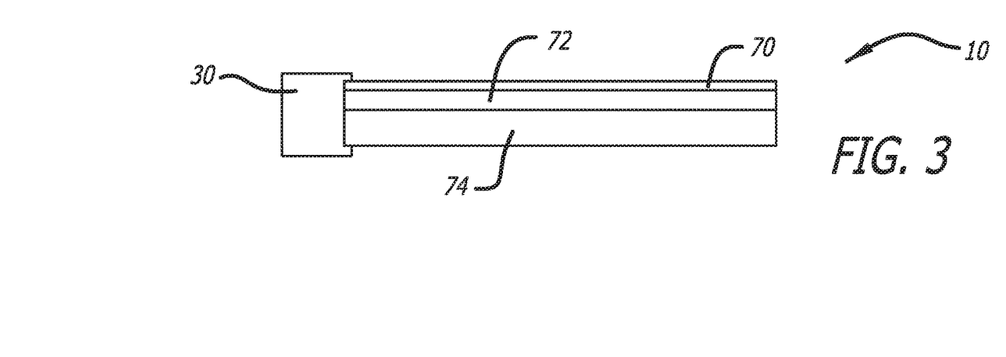
FIG. 3 is a sectional view of the embodiment of FIG. 1 taken along section lines 3-3.

FIG. 3 depicts a sectional view of the embodiment of the shield 10 taken along section lines 3-3 of FIG. 1. The section view of FIG. 3 shows the layered construction of the shield 10, and includes a transparent touchscreen layer 70, a transparent computer display 72, and a transparent radiation shield 74. The transparent computer display layer 72 may be any clear display technology, such as LED or LCD.

Figure 4:
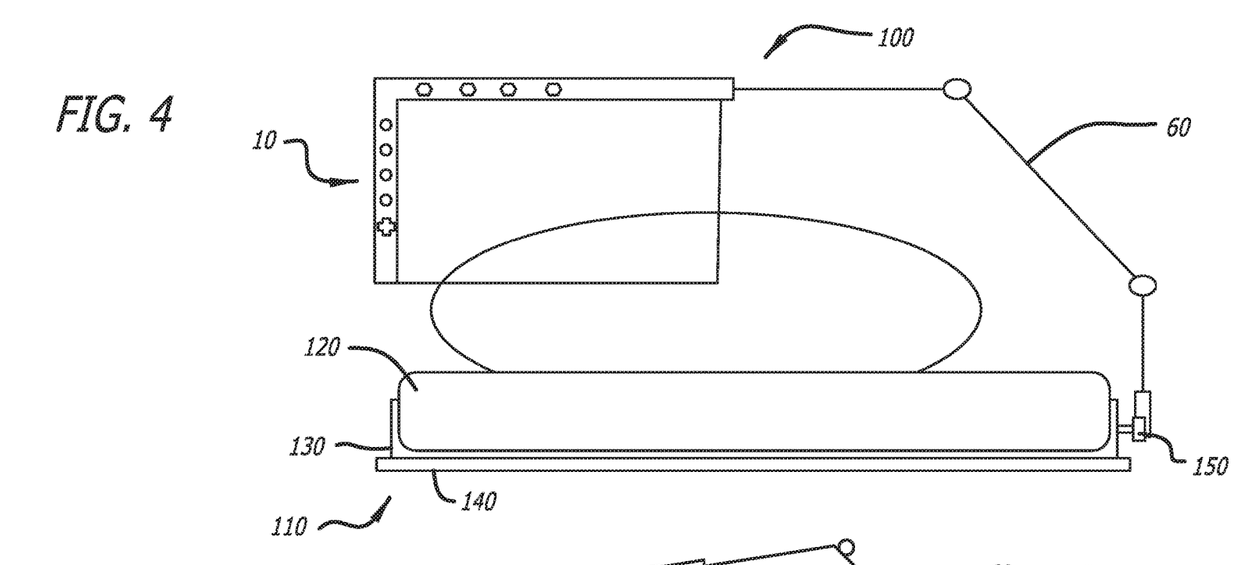
FIG. 4 is a front elevation of an embodiment of a system of the invention.
Figure 5:
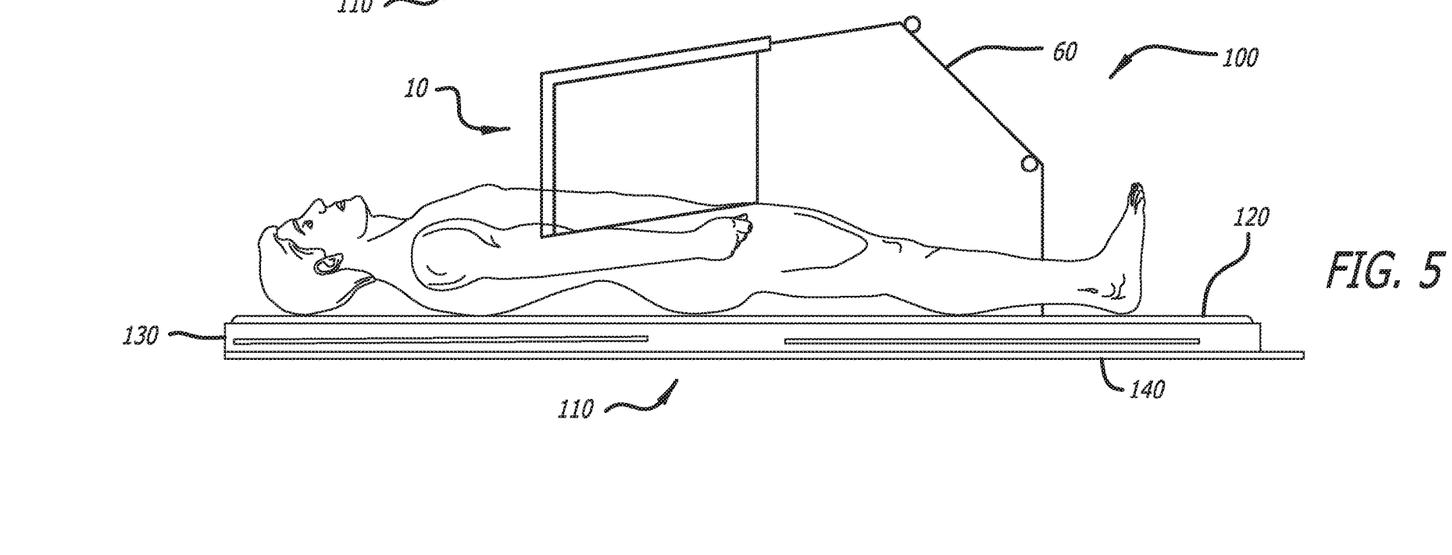
FIG. 5 is a perspective view of an embodiment of a system of the invention.

FIGS. 4 and 5 show an embodiment of a system 100 of the invention. System 100 includes the shield 10 and a patient platform 110, which in this case includes a mattress 120, a sled 130 and an x-ray table 140. The shield 10 is attached to the arm 60, which may be articulated as shown. The arm 60 is attached to an attachment rail 150 of the sled 130.

Figure 6:
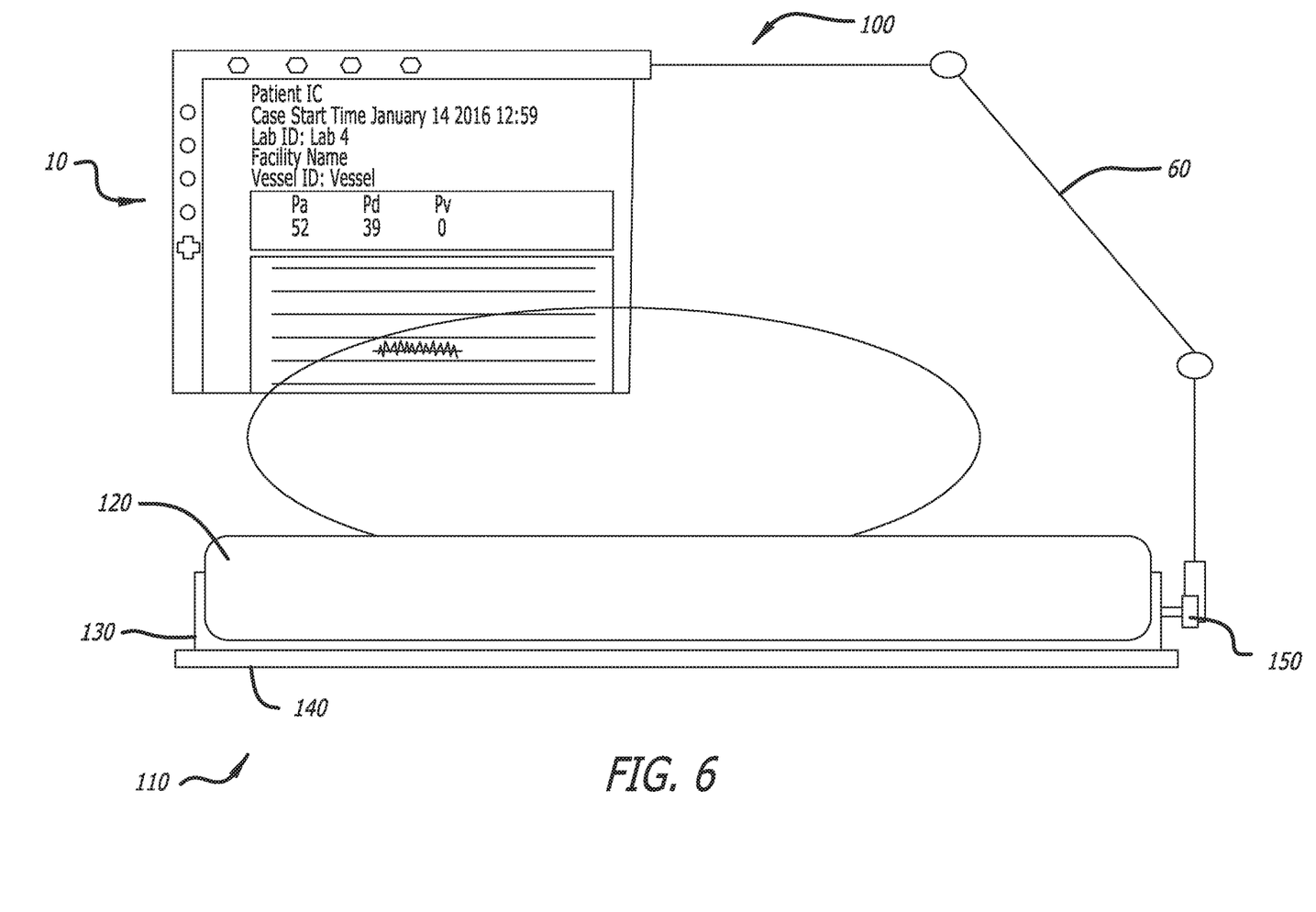
FIG. 6 is an end elevation of an embodiment of a system of the invention.
Figure 7:
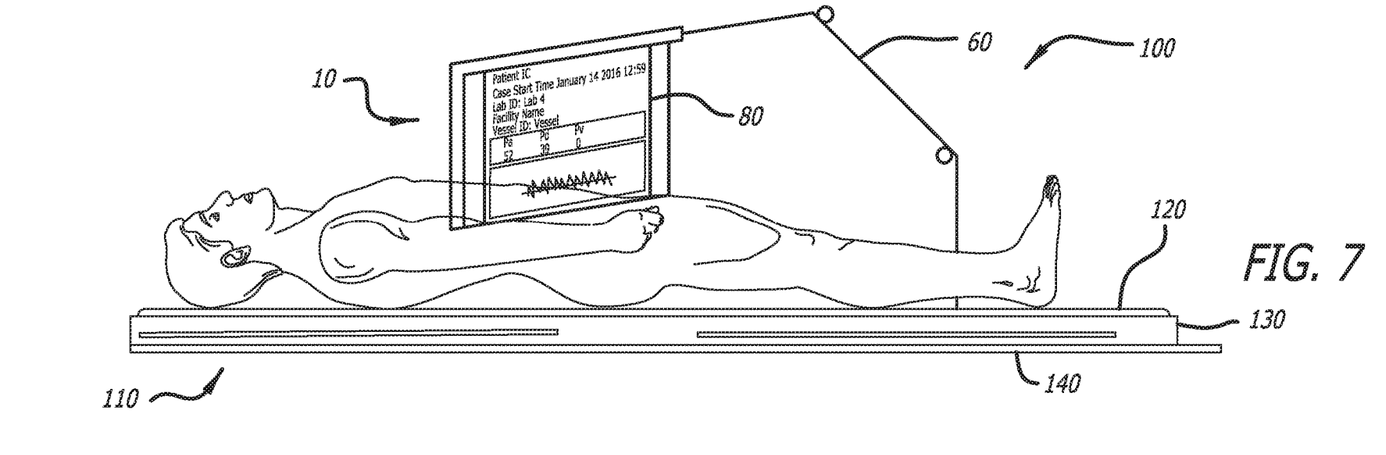
FIG. 7 is a perspective view of an embodiment of a system of the invention.

FIGS. 6 and 7 show an embodiment of a system 100 of the invention in which the transparent display 72 of the shield 10 is powered on and is displaying an overlay 80 that includes physiologic data. In at least one embodiment, the opacity of the overlay is adjustable such that the user can adjust how easy it is to see the patient through the display.

Figure 8:
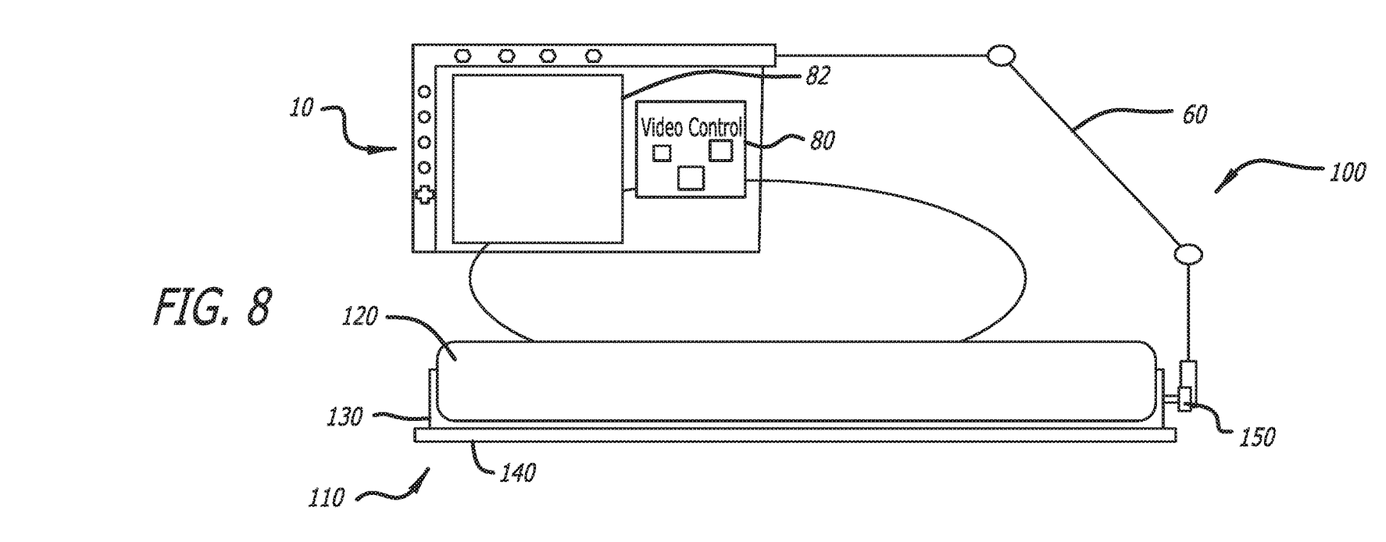
FIG. 8 is an end elevation of an embodiment of a system of the invention.
Figure 9:
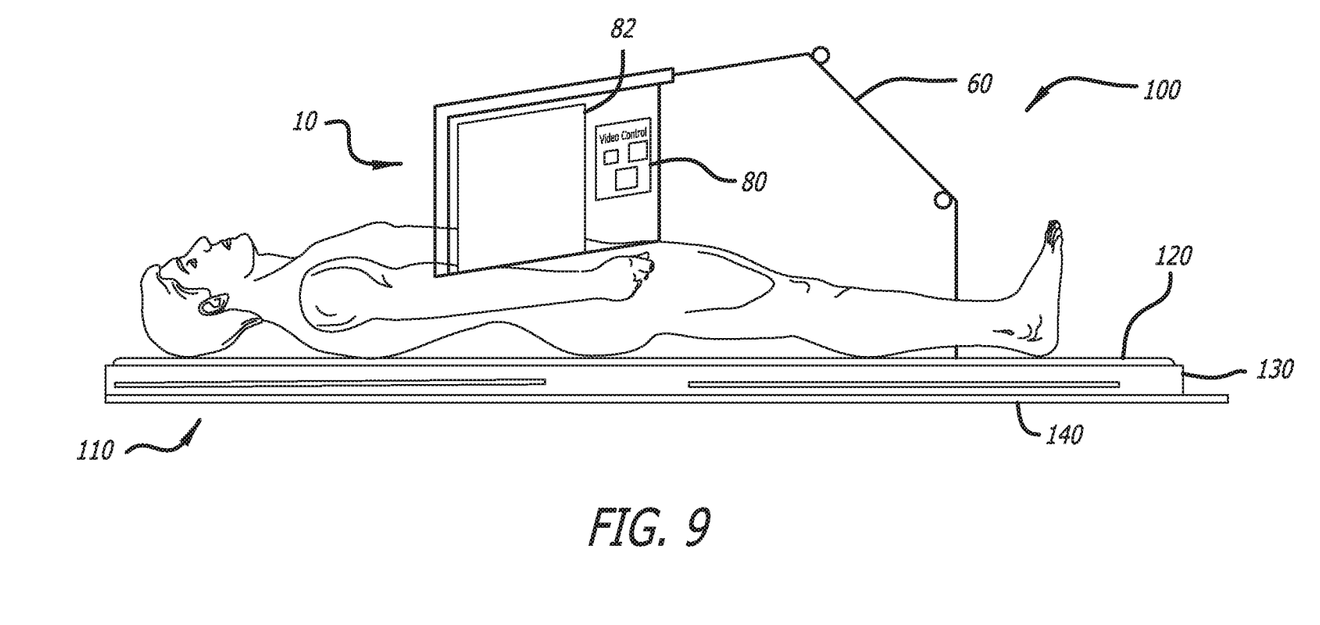
FIG. 9 is a perspective view of an embodiment of a system of the invention.

FIGS. 8 and 9 show an embodiment of a system 100 of the invention in which the transparent display 72 of the shield 10 is powered on and is displaying an overlay 80, including physiologic data, juxtaposed to a second window 82 showing imaging of the patient.

Figure 10:
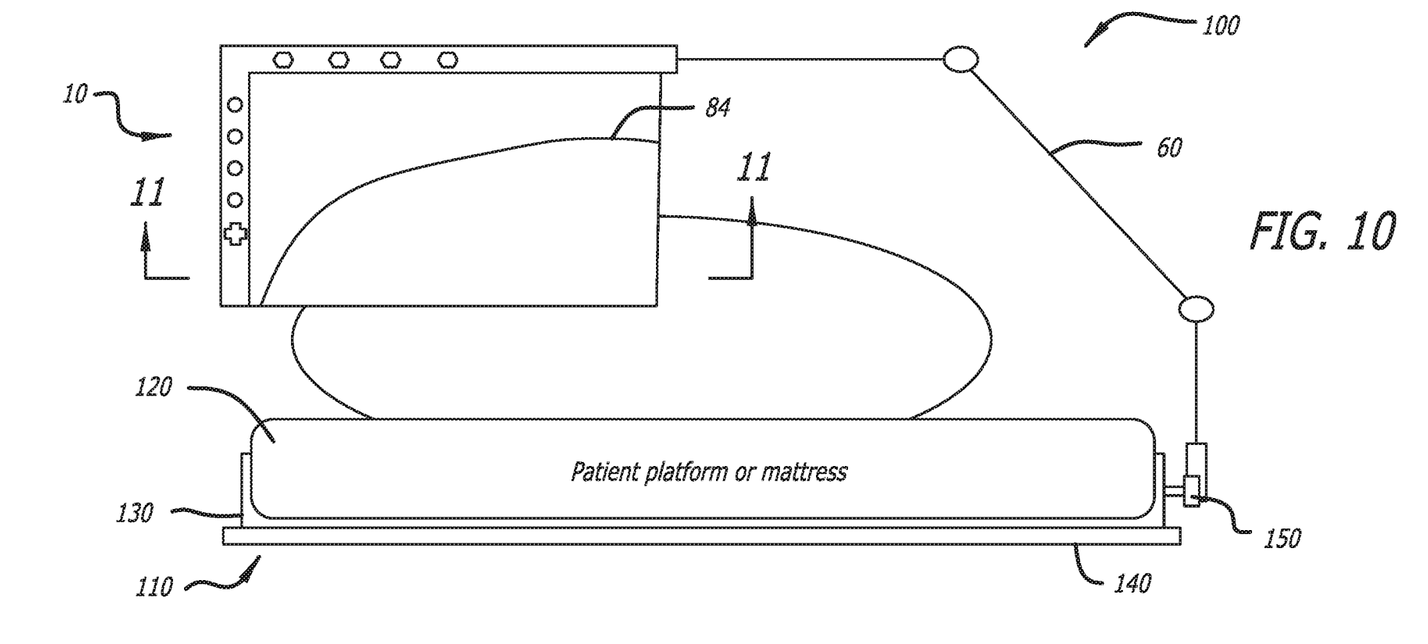
FIG. 10 is an end elevation of an embodiment of a system of the invention; and, FIG. 11 is a sectional view of the display of FIG. 10 taken along section lines 11-11.
Figure 11:
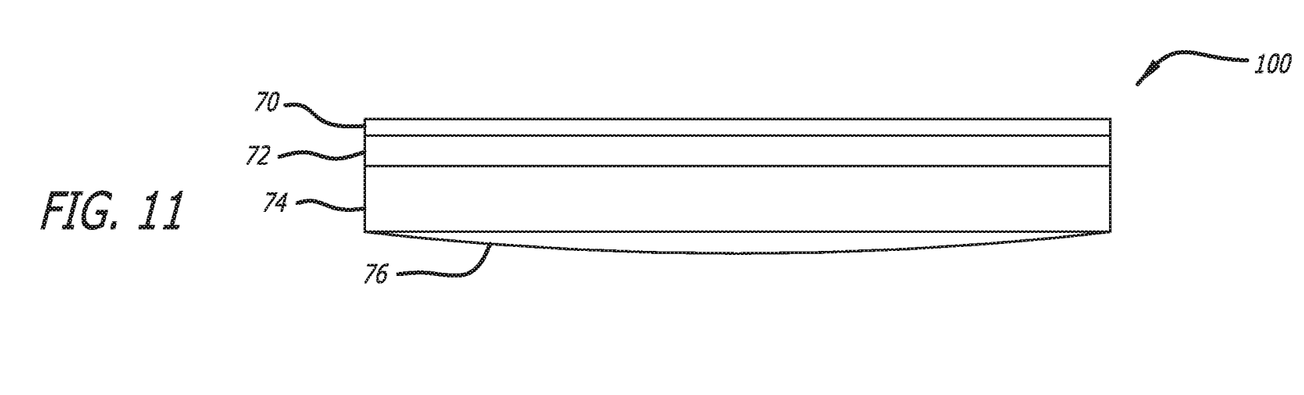

FIG. 10 shows an embodiment of a system 100 of the invention in which the shield 10 includes magnification feature 84. The magnification feature could be provided electronically, via a projected image using the camera and a zoom feature. Alternatively, as shown in FIG. 11. The magnification feature 84 includes a curved magnifying lens layer 76 placed onto the display 10. The transparent magnifying lens layer 76 may be permanently installed onto the display 10, or may be an adhesive layer applied to the display 10. It is also envisioned that the magnifying lens layer 76 be a flat Fresnel lens sheet applied to the display 10.

What is claimed is:

1. A radiation shield connectable for use with a patient platform comprising a plurality of layers, said plurality of layers including: an at least partially transparent display; and, an at least partially transparent radiation shield; wherein the at least partially transparent display comprises transparent computer display technology such that patient-related data fields are producible on the at least partially transparent display, allowing a user to view data on the display while simultaneously seeing a patient through the data fields, wherein the at least partially transparent display includes an adjustment control for changing an opacity of the patient-related data fields.

2. The radiation shield of claim 1 wherein the plurality of layers further includes an at least partially transparent touchscreen input layer that provides touch control of the patient-related data producible on the at least partially transparent display.

3. The radiation shield of claim 1 wherein the plurality of layers further includes an at least partially transparent magnification layer.

4. The radiation shield of claim 1 further comprising a plurality of controls usable to control features of the at least partially transparent display.

5. The radiation shield of claim 1 wherein data displayed in said patient-related data fields includes real-time diagnostic imaging fed to said display from a medical data source selected from the group including imaging machine, imaging device, medical sensor, electrocardiogram, blood pressure sensor, heart rate sensor, radiation dosimeter, ultrasonic imager, X-ray imager, arterial oxygen saturation sensor.

6. A system for use in tending to a medical patient comprising: a patient platform including: a mattress; a table; a radiation shield comprising a plurality of layers, said plurality of layers including: an at least partially transparent display; and, an at least partially transparent radiation shield; wherein the at least partially transparent display comprises transparent computer display technology such that patient-related data is producible in transparent data fields on the at least partially transparent display while the display is at least partially transparent; and, an arm connecting the shield to the patient platform; wherein the at least partially transparent display includes an adjustment control for changing an opacity of the patient-related data.

7. The system of claim 6 wherein the plurality of layers further includes an at least partially transparent touchscreen input layer that provides touch control of the patient-related data producible in the transparent data fields on the at least partially transparent display.

8. The system of claim 6 wherein the plurality of layers further includes an at least partially transparent magnification layer.

9. The system of claim 6 further comprising a plurality of controls usable to control features of the at least partially transparent display.

10. The system of claim 6 wherein said patient-related data includes real-time imaging fed to said display from an imaging machine.

11. The system of claim 6 further comprising a sled between said mattress and said table; said sled including an attachment point for attaching said arm to said patient platform.

12. The system of claim 6 wherein said table comprises an x-ray table.

13. The system of claim 6 wherein said arm is articulated such that said radiation shield may be positioned at a variety of orientations.

14. A method of protecting a physician while attending to a patient and using x-ray imaging: providing an at least partially transparent shield on an articulated arm such that said shield is positionable between the physician and the patient; displaying data on said at least partially transparent shield pertaining to the patient while being able to view the patient through the data displayed on the at least partially transparent shield, wherein the data displayed on the at least partially transparent shield includes a diagnostic image of the patient.

15. The method of claim 14 wherein displaying data on said shield comprises displaying images from an x-ray.

16. The method of claim 14 wherein displaying data on said shield comprises providing controls such that a physician can select the data being displayed.

17. The method of claim 16 wherein providing controls comprises providing touchscreen controls on said shield.

18. The method of claim 14 wherein the articulated arm is connected to a patient platform.

\* \* \* \* \*